US012779222B2

(12) United States Patent
Lee et al.

(10) Patent No.: US 12,779,222 B2
(45) Date of Patent: Nov. 3, 2026

(54) COCHLEAR IMPLANTS HAVING MRI-COMPATIBLE MAGNET ASSEMBLIES AND ASSOCIATED SYSTEMS

(71) Applicant: Advanced Bionics LLC, Valencia, CA (US)

(72) Inventors: Sung Jin Lee, Valencia, CA (US); James George Elcoate Smith, Santa Clarita, CA (US)

(73) Assignee: Advanced Bionics, LLC, Valencia, CA (US)

( * ) Notice: Subject to any disclaimer, the term of this patent is extended or adjusted under 35 U.S.C. 154(b) by 223 days.

(21) Appl. No.: 18/701,147

(22) PCT Filed: Feb. 24, 2022

(86) PCT No.: PCT/US2022/017784

§ 371 (c)(1),
(2) Date: Apr. 12, 2024

(87) PCT Pub. No.: WO2023/063983

PCT Pub. Date: Apr. 20, 2023

(65) Prior Publication Data

US 2025/0001175 A1 Jan. 2, 2025

Related U.S. Application Data

(63) Continuation-in-part of application No. 17/499,813, filed on Oct. 12, 2021, now Pat. No. 12,440,668.

(51) Int. Cl.
*A61N 1/375* (2006.01)
*A61N 1/05* (2006.01)
*A61N 1/36* (2006.01)

(52) U.S. Cl.
CPC ....... *A61N 1/36038* (2017.08); *A61N 1/0541* (2013.01); *A61N 1/375* (2013.01)

(58) Field of Classification Search
CPC .................. A61N 1/36038; A61N 1/375–3758
See application file for complete search history.

(56) References Cited

U.S. PATENT DOCUMENTS 4,214,366 A 7/1980 Laban
4,352,960 A 10/1982 Dormer et al.
(Continued)

FOREIGN PATENT DOCUMENTS

CN 212542072 U 2/2021
DE 202006017662 U1 9/2007
(Continued)

OTHER PUBLICATIONS

PCT International Search and Written Opinion dated Jun. 29, 2022 for PCT App. Ser. No. PCT/US2022/017784.
(Continued)

*Primary Examiner* — George R Evanisko
(74) *Attorney, Agent, or Firm* — Henricks Slavin LLP

(57) ABSTRACT

A magnet assembly in accordance with at least one of the present inventions may include a case defining a central axis and including first and second end walls and a side wall, with an inner surface, between the first and second end walls, a frame within the case and rotatable about the central axis of the case, a plurality of diametrically magnetized magnets that are located in the frame, that each define a longitudinal axis and a N-S direction, and that are rotatable about the longitudinal axis relative to the frame, and a ring, defining an outer surface, between the frame and the case side wall and offset from the case side wall such that a first air gap is located between the inner surface of the case side wall and the outer surface of the ring.

17 Claims, 5 Drawing Sheets

(56) References Cited

U.S. PATENT DOCUMENTS

| | | | |
|---|---|---|---|
| 4,595,390 | A | 6/1986 | Hakim et al. |
| 4,606,329 | A | 8/1986 | Hough |
| 4,612,915 | A | 9/1986 | Hough et al. |
| 4,618,949 | A | 10/1986 | Lister |
| RE32,947 | E | 6/1989 | Dormer et al. |
| 5,290,281 | A | 3/1994 | Tschakaloff |
| 5,755,762 | A | 5/1998 | Bush |
| 5,824,022 | A | 10/1998 | Zilberman et al. |
| 5,945,762 | A | 8/1999 | Chen et al. |
| 6,032,677 | A | 3/2000 | Blechman et al. |
| 6,178,353 | B1 | 1/2001 | Griffith et al. |
| 6,190,305 | B1 | 2/2001 | Ball et al. |
| 6,217,508 | B1 | 4/2001 | Ball et al. |
| 6,227,820 | B1 | 5/2001 | Jarvik |
| 6,292,678 | B1 | 9/2001 | Hall et al. |
| 6,348,070 | B1 | 2/2002 | Teissl et al. |
| 6,358,281 | B1 | 3/2002 | Berrang et al. |
| 6,461,288 | B1 | 10/2002 | Holcomb |
| 6,599,321 | B2 | 7/2003 | Hyde, Jr. |
| 6,838,963 | B2 | 1/2005 | Zimmerling |
| 7,091,806 | B2 | 8/2006 | Zimmerling et al. |
| 7,190,247 | B2 | 3/2007 | Zimmerling |
| 7,266,208 | B2 | 9/2007 | Charvin et al. |
| 7,566,296 | B2 | 7/2009 | Zimmerling et al. |
| 7,609,061 | B2 | 10/2009 | Hochmair |
| 7,642,887 | B2 | 1/2010 | Zimmerling |
| 7,680,525 | B1 | 3/2010 | Damadian |
| 7,729,774 | B1 | 6/2010 | Lynch et al. |
| 7,774,069 | B2 | 8/2010 | Olson et al. |
| 7,856,986 | B2 | 12/2010 | Darley |
| 7,881,800 | B2 | 2/2011 | Daly et al. |
| 7,976,453 | B2 | 7/2011 | Zimmerling et al. |
| 8,013,699 | B2 | 9/2011 | Zimmerling |
| 8,027,735 | B1 | 9/2011 | Tziviskos et al. |
| 8,118,725 | B2 | 2/2012 | Zimmerling et al. |
| 8,255,058 | B2 | 8/2012 | Gibson et al. |
| 8,340,774 | B2 | 12/2012 | Hochmair et al. |
| 8,634,909 | B2 | 1/2014 | Zimmerling et al. |
| 8,733,494 | B1 | 5/2014 | Leigh |
| 8,734,475 | B2 | 5/2014 | Ekvall et al. |
| 8,744,106 | B2 | 6/2014 | Ball |
| 8,758,394 | B2 | 6/2014 | Zimmerling et al. |
| 8,787,608 | B2 | 7/2014 | Van Himbeeck et al. |
| 8,790,409 | B2 | 7/2014 | Van den Heuvel et al. |
| 8,825,171 | B1 | 9/2014 | Thenuwara et al. |
| 8,891,795 | B2 | 11/2014 | Andersson |
| 8,897,475 | B2 | 11/2014 | Ball et al. |
| RE45,701 | E | 9/2015 | Zimmerling et al. |
| 9,126,010 | B2 | 9/2015 | Shah et al. |
| 9,162,054 | B2 | 10/2015 | Dalton |
| 9,227,064 | B2 | 1/2016 | Duftner |
| 9,295,425 | B2 | 3/2016 | Ball |
| 9,314,625 | B2 | 4/2016 | Kasic, II et al. |
| 9,352,149 | B2 | 5/2016 | Thenuwara et al. |
| RE46,057 | E | 7/2016 | Zimmerling et al. |
| 9,392,382 | B1 | 7/2016 | Nagl et al. |
| 9,420,388 | B2 | 8/2016 | Ball |
| 9,549,267 | B2 | 1/2017 | Nagl et al. |
| 9,615,181 | B2 | 4/2017 | Nagl et al. |
| 9,656,065 | B2 | 5/2017 | Tourrel et al. |
| 9,884,197 | B2 | 2/2018 | Lehmann et al. |
| 9,919,154 | B2 | 3/2018 | Lee |
| 9,931,501 | B2 | 4/2018 | Smyth |
| 10,300,276 | B2 | 5/2019 | Lee et al. |
| 10,463,849 | B2 | 11/2019 | Lee et al. |
| 10,532,209 | B2 | 1/2020 | Lee et al. |
| 10,646,712 | B2 | 5/2020 | Smith et al. |
| 10,646,718 | B2 | 5/2020 | Smith et al. |
| 10,806,936 | B2 | 10/2020 | Crawford et al. |
| 10,821,279 | B2 | 11/2020 | Lee et al. |
| 11,097,095 | B2 | 8/2021 | Smith et al. |
| 11,287,495 | B2 | 3/2022 | Smith et al. |
| 11,304,015 | B2 | 4/2022 | Haagerup |
| 11,364,384 | B2 | 6/2022 | Smith et al. |
| 11,471,679 | B2 | 10/2022 | Smith et al. |
| 11,476,025 | B2 | 10/2022 | Lee et al. |
| 11,529,212 | B2 * | 12/2022 | Prescott ................. A61B 90/90 |
| 11,638,823 | B2 | 5/2023 | Brehm et al. |
| 11,752,338 | B2 | 9/2023 | Smith et al. |
| 11,779,754 | B2 | 10/2023 | Smith et al. |
| 11,986,656 | B2 | 5/2024 | Lee et al. |
| 12,350,493 | B2 | 7/2025 | Smith et al. |
| 12,364,857 | B2 | 7/2025 | Crawford et al. |
| 12,440,668 | B2 | 10/2025 | Lee et al. |
| 12,544,579 | B2 | 2/2026 | Smith et al. |
| 2004/0012470 | A1 | 1/2004 | Zimmerling et al. |
| 2004/0059423 | A1 | 3/2004 | Barnes et al. |
| 2004/0063072 | A1 | 4/2004 | Honkura et al. |
| 2004/0210103 | A1 | 10/2004 | Westerkull |
| 2004/0260362 | A1 | 12/2004 | Darley |
| 2005/0001703 | A1 | 1/2005 | Zimmerling |
| 2005/0004629 | A1 | 1/2005 | Gibson et al. |
| 2005/0062567 | A1 | 3/2005 | Zimmerling et al. |
| 2006/0015155 | A1 | 1/2006 | Charvin et al. |
| 2006/0116743 | A1 | 6/2006 | Gibson et al. |
| 2006/0244560 | A1 | 11/2006 | Zimmerling et al. |
| 2007/0053536 | A1 | 3/2007 | Westerkull |
| 2007/0126540 | A1 | 6/2007 | Zimmerling |
| 2008/0097496 | A1 | 4/2008 | Chang et al. |
| 2008/0103350 | A1 | 5/2008 | Farone |
| 2008/0192968 | A1 | 8/2008 | Ho et al. |
| 2008/0195178 | A1 | 8/2008 | Kuzma |
| 2009/0048580 | A1 | 2/2009 | Gibson |
| 2009/0099403 | A1 | 4/2009 | Zimmerling et al. |
| 2009/0134721 | A1 | 5/2009 | Zimmerling |
| 2009/0248155 | A1 | 10/2009 | Parker |
| 2009/0287278 | A1 | 11/2009 | Charvin |
| 2010/0004716 | A1 | 1/2010 | Zimmerling et al. |
| 2010/0036458 | A1 | 2/2010 | Dufter et al. |
| 2010/0046778 | A1 | 2/2010 | Crawford et al. |
| 2010/0046779 | A1 | 2/2010 | Crawford et al. |
| 2011/0009925 | A1 | 1/2011 | Leigh et al. |
| 2011/0022120 | A1 | 1/2011 | Ball et al. |
| 2011/0068885 | A1 | 3/2011 | Fullerton et al. |
| 2011/0218605 | A1 | 9/2011 | Cryer |
| 2011/0224756 | A1 | 9/2011 | Zimmerling et al. |
| 2011/0255731 | A1 | 10/2011 | Ball |
| 2011/0264172 | A1 | 10/2011 | Zimmerling et al. |
| 2012/0296155 | A1 | 11/2012 | Ball |
| 2013/0079749 | A1 | 3/2013 | Overstreet et al. |
| 2013/0150657 | A1 | 6/2013 | Leigh et al. |
| 2013/0184804 | A1 | 7/2013 | Dalton |
| 2013/0281764 | A1 | 10/2013 | Bjorn et al. |
| 2013/0343588 | A1 | 12/2013 | Karunasiri |
| 2014/0005750 | A1 | 1/2014 | Garnham et al. |
| 2014/0012069 | A1 | 1/2014 | Ball |
| 2014/0012070 | A1 | 1/2014 | Nagl et al. |
| 2014/0012071 | A1 | 1/2014 | Nagl et al. |
| 2014/0012349 | A1 | 1/2014 | Zimmerling |
| 2014/0121449 | A1 | 5/2014 | Kasic et al. |
| 2014/0121586 | A1 | 5/2014 | Bertrand et al. |
| 2014/0163692 | A1 | 6/2014 | Van den Heuvel et al. |
| 2014/0336447 | A1 | 11/2014 | Bjorn et al. |
| 2014/0343626 | A1 | 11/2014 | Thenuwara et al. |
| 2015/0025613 | A1 | 1/2015 | Nyberg, II et al. |
| 2015/0073205 | A1 | 3/2015 | Ball et al. |
| 2015/0087892 | A1 | 3/2015 | Tourrel et al. |
| 2015/0094521 | A1 | 4/2015 | Neuman et al. |
| 2015/0100109 | A1 | 4/2015 | Feldman et al. |
| 2015/0112407 | A1 | 4/2015 | Hartley et al. |
| 2015/0265842 | A1 | 9/2015 | Ridler |
| 2015/0320523 | A1 | 11/2015 | Way et al. |
| 2015/0367126 | A1 | 12/2015 | Smyth |
| 2015/0374989 | A1 | 12/2015 | Hazard et al. |
| 2015/0382114 | A1 | 12/2015 | Andersson et al. |
| 2016/0008596 | A1 | 1/2016 | Gibson et al. |
| 2016/0023006 | A1 | 1/2016 | Ridler et al. |
| 2016/0037273 | A1 | 2/2016 | Gustafsson |
| 2016/0144170 | A1 | 5/2016 | Gibson et al. |
| 2016/0205484 | A1 | 7/2016 | Nagl et al. |
| 2016/0213936 | A1 | 7/2016 | Heerlein et al. |
| 2016/0310737 | A1 | 10/2016 | Tourrel et al. |
| 2016/0361537 | A1 | 12/2016 | Leigh et al. |
| 2016/0381473 | A1 | 12/2016 | Gustafsson |

(56) References Cited

U.S. PATENT DOCUMENTS

| | | | | |
|---|---|---|---|---|
| 2016/0381474 | A1 | 12/2016 | Gustafsson et al. | |
| 2017/0050027 | A1 | 2/2017 | Andersson et al. | |
| 2017/0078808 | A1 | 3/2017 | Kennes | |
| 2017/0156010 | A1 | 6/2017 | Verma et al. | |
| 2017/0173334 | A1 | 6/2017 | Zimmerling | |
| 2017/0239476 | A1 | 8/2017 | Lee | |
| 2017/0251312 | A1 | 8/2017 | Crawford et al. | |
| 2017/0347208 | A1 | 11/2017 | Jurkiewicz | |
| 2018/0028818 | A1 | 2/2018 | Anderson et al. | |
| 2018/0056084 | A1 | 3/2018 | Alam | |
| 2018/0110985 | A1 | 4/2018 | Walter | |
| 2018/0110986 | A1 | 4/2018 | Lee | |
| 2018/0133486 | A1 | 5/2018 | Smith | |
| 2018/0146308 | A1 | 5/2018 | Leigh et al. | |
| 2018/0160241 | A1 | 6/2018 | Gustafsson et al. | |
| 2018/0160242 | A1 | 6/2018 | Sriskandarajah | |
| 2018/0185634 | A1 | 7/2018 | Smyth | |
| 2018/0249262 | A1 | 8/2018 | Santek | |
| 2018/0270591 | A1 | 9/2018 | Kennes | |
| 2018/0296826 | A1 | 10/2018 | Lee et al. | |
| 2018/0303602 | A1 | 10/2018 | Leigh | |
| 2018/0304078 | A1 | 10/2018 | Crawford et al. | |
| 2018/0369586 | A1 | 12/2018 | Lee et al. | |
| 2019/0015662 | A1 | 1/2019 | Raje et al. | |
| 2019/0046797 | A1 | 2/2019 | Calixto et al. | |
| 2019/0053908 | A1 | 2/2019 | Cook et al. | |
| 2019/0076649 | A1 | 3/2019 | Lee et al. | |
| 2019/0255316 | A1 | 8/2019 | Lee et al. | |
| 2019/0298417 | A1 | 10/2019 | Barrett et al. | |
| 2020/0114151 | A1 | 4/2020 | Smith et al. | |
| 2020/0230422 | A1 | 7/2020 | Gibson et al. | |
| 2020/0238088 | A1 | 7/2020 | Smith et al. | |
| 2020/0330777 | A1 | 10/2020 | Smith et al. | |
| 2020/0391023 | A1* | 12/2020 | Lee .................... | A61N 1/36038 |
| 2021/0046311 | A1 | 2/2021 | Brehm et al. | |
| 2021/0106815 | A1 | 4/2021 | Smith et al. | |
| 2021/0156934 | A1 | 5/2021 | Smith et al. | |
| 2021/0196961 | A1* | 7/2021 | Louwagie .............. | A61N 1/378 |
| 2021/0299456 | A1 | 9/2021 | Smith et al. | |
| 2021/0316136 | A1 | 10/2021 | Smith et al. | |
| 2021/0339021 | A1 | 11/2021 | Brehm et al. | |
| 2022/0273948 | A1 | 9/2022 | Calixto et al. | |
| 2022/0280793 | A1 | 9/2022 | Smith et al. | |
| 2023/0032218 | A1 | 2/2023 | Smith et al. | |
| 2023/0061335 | A1 | 3/2023 | Lee et al. | |
| 2023/0115968 | A1 | 4/2023 | Lee et al. | |
| 2024/0342473 | A1 | 10/2024 | Smith et al. | |
| 2025/0001186 | A1 | 1/2025 | Lee et al. | |
| 2025/0050102 | A1 | 2/2025 | Smith et al. | |
| 2026/0054068 | A1 | 2/2026 | Smith et al. | |
| 2026/0077195 | A1 | 3/2026 | Alanis et al. | |

FOREIGN PATENT DOCUMENTS

| | | | |
|---|---|---|---|
| EP | 0241307 | A2 | 10/1987 |
| EP | 2117489 | B1 | 5/2010 |
| EP | 2853287 | A1 | 4/2015 |
| EP | 2560730 | B1 | 11/2016 |
| EP | 3138605 | A1 | 3/2017 |
| EP | 2098198 | B1 | 9/2017 |
| EP | 3964259 | A1 | 3/2022 |
| RU | 2727227 | C1 | 7/2020 |
| WO | WO9858990 | A1 | 12/1998 |
| WO | WO03081976 | A2 | 10/2003 |
| WO | WO03092326 | A1 | 11/2003 |
| WO | WO2004004416 | A1 | 1/2004 |
| WO | WO2004014269 | A1 | 2/2004 |
| WO | WO2004014270 | A1 | 2/2004 |
| WO | WO2007024657 | A2 | 3/2007 |
| WO | WO2009124045 | A1 | 10/2009 |
| WO | WO2009124174 | A2 | 10/2009 |
| WO | WO2009149069 | A2 | 12/2009 |
| WO | WO2010000027 | A1 | 1/2010 |
| WO | WO2010083554 | A1 | 7/2010 |
| WO | WO2011011409 | A1 | 1/2011 |
| WO | WO2011109486 | A2 | 9/2011 |
| WO | WO2011133747 | A1 | 10/2011 |
| WO | WO2012010195 | A1 | 1/2012 |
| WO | WO2013043176 | A1 | 3/2013 |
| WO | WO2013063355 | A1 | 5/2013 |
| WO | WO2014011441 | A1 | 1/2014 |
| WO | WO2014011582 | A2 | 1/2014 |
| WO | WO2014046662 | A1 | 3/2014 |
| WO | WO2014164023 | A1 | 10/2014 |
| WO | WO2015065442 | A1 | 5/2015 |
| WO | WO2016016821 | A1 | 2/2016 |
| WO | WO2016190886 | A1 | 12/2016 |
| WO | WO2016191429 | A1 | 12/2016 |
| WO | WO2016207856 | A1 | 12/2016 |
| WO | WO2017027045 | A1 | 2/2017 |
| WO | WO2017027046 | A1 | 2/2017 |
| WO | WO2017029615 | A1 | 2/2017 |
| WO | WO2017034530 | A1 | 3/2017 |
| WO | WO2017046650 | A1 | 3/2017 |
| WO | WO2017087004 | A1 | 5/2017 |
| WO | WO2017105510 | A1 | 6/2017 |
| WO | WO2017105511 | A1 | 6/2017 |
| WO | WO2017105604 | A1 | 6/2017 |
| WO | WO2017172566 | A1 | 10/2017 |
| WO | WO2018190813 | A1 | 10/2018 |
| WO | WO2018191314 | A1 | 10/2018 |
| WO | WO2018199936 | A1 | 11/2018 |
| WO | WO2018200347 | A1 | 11/2018 |
| WO | WO2018217187 | A1 | 11/2018 |
| WO | WO2019027745 | A1 | 2/2019 |
| WO | WO2019083540 | A1 | 5/2019 |
| WO | WO2019160555 | A1 | 8/2019 |
| WO | WO2020092185 | A1 | 5/2020 |
| WO | WO2021201845 | A1 | 10/2021 |
| WO | WO2023063934 | A1 | 4/2023 |
| WO | WO2023063983 | A1 | 4/2023 |
| WO | WO2023064308 | A1 | 4/2023 |
| WO | WO2023113790 | A1 | 6/2023 |
| WO | WO2024043896 | A1 | 2/2024 |
| WO | WO2024080978 | A1 | 4/2024 |

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.

Teissl et al., "Magentic Resonance Imaging and Cochlear Implants: Compatibility and Safety Aspects," Journal of Magnetic Resonance Imaging, Society for Magnetic Resonance Imaging, vol. 9, No. 1, pp. 26-38, Jan. 1, 1999.

* cited by examiner

COCHLEAR IMPLANTS HAVING MRI-COMPATIBLE MAGNET ASSEMBLIES AND ASSOCIATED SYSTEMS

CROSS-REFERENCE TO RELATED APPLICATIONS

This application is the U.S. National Stage of PCT App. Ser. No. PCT/US2022/017784, filed Feb. 24, 2022, which is a continuation-in-part of, and claims priority to, U.S. application Ser. No. 17/499,813, filed Oct. 12, 2021, now U.S. Pat. No. 12,440,668, which is incorporated herein by reference in its entirety.

BACKGROUND

1. Field

The present disclosure relates generally to implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ Cl Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing. The skin and subcutaneous tissue that separates the headpiece magnet and implant magnet is sometimes referred to as the "skin flap," which is frequently 3 mm to 11 mm thick.

The present inventors have determined that conventional cochlear implants and stimulation systems are susceptible to improvement. For example, the magnet in some conventional cochlear implant is a disk-shaped axially magnetized magnet that has north and south magnetic dipoles which are aligned in the axial direction of the disk. Such magnets are not compatible with magnetic resonance imaging ("MRI") systems, and may have to be surgically removed from the cochlear the implant prior to the MRI procedure and then surgically replaced thereafter. Other cochlear implants include a diametrically magnetized disk-shaped magnet that is rotatable relative to the remainder of the implant about its central axis, and that has a N-S orientation which is perpendicular to the central axis. The present inventors have determined that diametrically magnetized disk-shaped magnets are less than optimal because a dominant magnetic field, such as the MRI magnetic field, that is misaligned by at least 30° or more from the N-S direction of the magnet may demagnetize the magnet or generate an amount of torque on the magnet that is sufficient to dislodge or reverse the magnet and/or dislocate the associated cochlear implant and/or cause excessive discomfort to the patient.

More recently, cochlear implants with MRI-compatible magnet assemblies have been introduced. The MRI-compatible magnet assemblies have a metal case defining a central axis, a frame within the case that is rotatable relative to the case about the central axis, and three or more elongate diametrically magnetized magnets that are rotatable about their respective longitudinal axis relative to the frame. This combination allows the magnets to align with three-dimensional (3D) MRI magnetic fields, regardless of field direction, which results in very low amounts of torque on the magnets. The case is hermetically sealed by welding (e.g., laser welding) the case cover to the case base after the frame and magnets are positioned therein. Examples of such MRI-compatible magnet assemblies may be found in U.S. Pat. Nos. 9,919,154, 10,463,849, and 10,532,209. Another proposed magnet assembly, which includes a single elongate magnet, is described in PCT Pat. Pub. No. 2020/092185 A1.

Although such MRI-compatible magnet assemblies have proven to be a significant advance in the art, the present inventors have determined that they are susceptible to improvement. For example, although plastic frames (e.g., injection molded plastic frames) are desirable due to their relatively low cost, as compared to metal frames, plastic frames are susceptible to being damaged by the heat associated with the welding of the case cover to the case base.

SUMMARY

A magnet assembly in accordance with at least one of the present inventions may include a case defining a central axis and including first and second end walls and a side wall, with an inner surface, between the first and second end walls, a frame within the case and rotatable about the central axis of the case, a plurality of diametrically magnetized magnets that are located in the frame, that each define a longitudinal axis and a N-S direction, and that are rotatable about the longitudinal axis relative to the frame, and a ring, defining an outer surface, between the frame and the case side wall and offset from the case side wall such that a first air gap is located between the inner surface of the case side wall and the outer surface of the ring. The present inventions also include cochlear implants including such a magnet assembly.

A magnet assembly in accordance with at least one of the present inventions may include a case defining a central axis and including a base and a cover that are secured to one another with weld, a frame within the case and rotatable about the central axis of the case, a plurality of diametrically magnetized magnets that are located in the frame, that each define a longitudinal axis and a N-S direction, and that are rotatable about the longitudinal axis relative to the frame, and means for thermally insulating the frame from heat associated with welding the base and cover to one another. The present inventions also include cochlear implants including such a magnet assembly.

A method in accordance with at least one of the present inventions may includes placing a frame and a plurality of diametrically magnetized magnets into a case that includes a base with a first end wall and a first side wall portion and cover with a second end wall and a second side wall portion, the first and second side wall portions defining respective inner surfaces, creating an air gap between the frame and the inner surfaces of the case side wall portions, and welding the side wall portions to one another after the frame and the plurality of diametrically magnetized magnets have been placed into the case and the air gap has been created.

There are a number of advantages associated with such magnet assemblies and methods. By way of example, but not limitation, the air gap or other thermal insulation protects the frame and magnets from heat associated with the welding of the case.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

Figure 1:
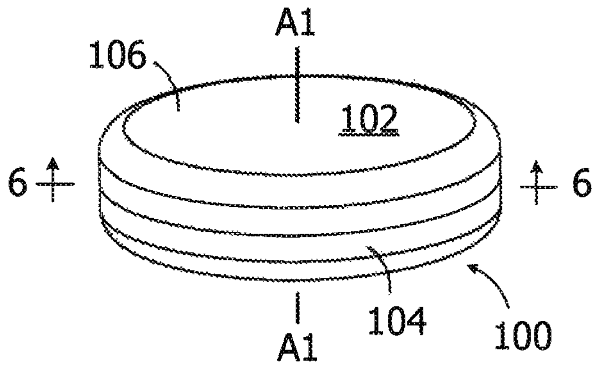
FIG. 1 is a perspective view of an implant magnet assembly in accordance with one embodiment of a present invention.
Figure 2:
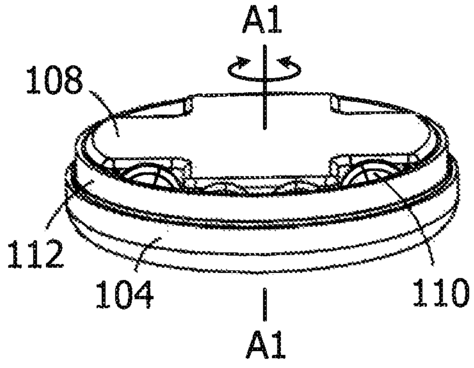
FIG. 2 is a perspective view of a portion of the implant magnet assembly illustrated in FIG. 1.
Figure 3:
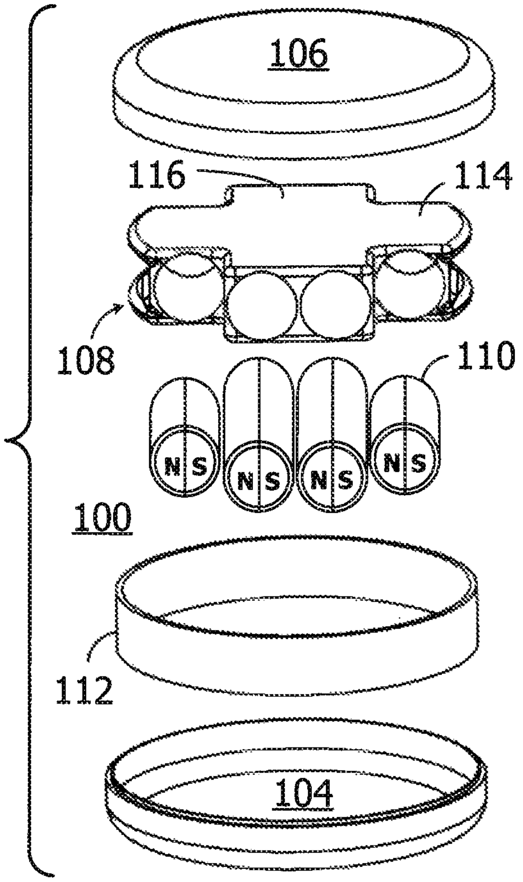
FIG. 3 is an exploded perspective view of the implant magnet assembly illustrated in FIG. 1.

The following is a detailed description of the best presently known modes of carrying out the inventions. This description is not to be taken in a limiting sense, but is made merely for the purpose of illustrating the general principles of the inventions.

As illustrated for example in FIGS. 1-5, an exemplary magnet assembly 100 includes a case 102, with base 104 and a cover 106, a frame 108 that is rotatable relative to the case, four elongate diametrically magnetized magnets 110 that are rotatable relative to the frame, and a ring 112 that is part of the thermal insulation arrangement discussed below with reference to FIG. 8. The magnet assembly 100 may, in some instances, be employed in a cochlear implant and in a system that includes such a cochlear implant in combination with a headpiece or other external device, as is described below with reference to FIGS. 15 and 16.

The case 102 in the exemplary magnet assembly 100 is disk-shaped and defines a central axis A1, which is also the central axis of the frame 108. The frame 108 is rotatable relative to the case 102 about the central axis A1 over 360°. The magnets 110 rotate with the frame 108 about the central axis A1. Each magnet 110 is also rotatable relative to the frame 108 about its own longitudinal axis A2 (also referred to as "axis A2") over 360°. In the exemplary implementation illustrated in FIGS. 1-5, the longitudinal axes A2 are parallel to one another and are perpendicular to the central axis A1. In other implementations, the magnets may be oriented such that the longitudinal axes thereof are at least substantially perpendicular to the central axis A1. As used herein, an axis that is "at least substantially perpendicular to the central axis" includes axes that are perpendicular to the central axis as well as axes that are slightly non-perpendicular to the central axis (i.e., axes that are offset from perpendicular by up to 5 degrees).

The exemplary case 102 is not limited to any particular configuration, size or shape. In the illustrated implementation, the case 102 is a two-part structure that includes the base 104 and the cover 106 which are secured to one another in such a manner that a hermetic seal is formed between the cover and the base. Suitable techniques for securing the cover 106 to the base 104 include, for example, seam welding with a laser welder. With respect to materials, the case 102 may be formed from biocompatible paramagnetic metals, such as titanium or titanium alloys. In particular, exemplary metals include commercially pure titanium (e.g., Grade 2) and the titanium alloy Ti-6Al-4V (Grade 5), while exemplary metal thicknesses may range from 0.20 mm to 0.25 mm. With respect to size and shape, the case 102 may have an overall size and shape similar to that of conventional cochlear implant magnets so that the magnet assembly 100 can be substituted for a conventional magnet in an otherwise conventional cochlear implant. The case 102 may also have an overall size and shape that is larger than that of conventional cochlear implant magnets in other embodiments. In some implementations, the diameter that may range from about 9 mm to about 16 mm and the thickness may range from about 1.5 mm to about 3.5 mm. The diameter of the case 102 in the illustrated embodiment is about 12.9 mm and the thickness is about 3.1 mm. As used herein, the word "about" means±10%.

Figure 5:
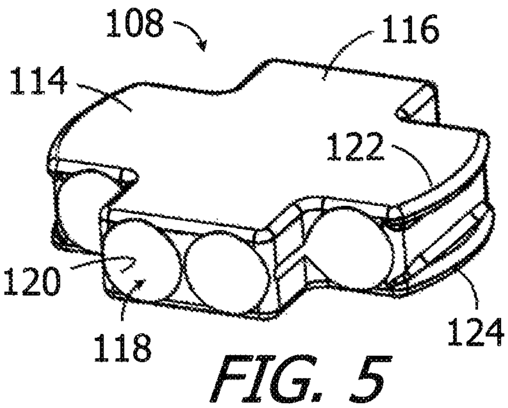
FIG. 5 is a perspective view of a portion of the implant magnet assembly illustrated in FIG. 1.

Referring more specifically to FIG. 5, the exemplary frame 108 includes a pair of relatively short rectangular portions 114 that are separated by a relatively long rectangular portion 116. The exemplary frame 108 also includes a plurality of receptacles 118 are defined by tubular walls 120. Two of the receptacles 118 are relatively short and are respectively located within the two relatively short rectangular portions 114, and two of the receptacles 118 are relatively long and are located within the relatively long rectangular portion 116. The elongate diametrically magnetized magnets 110 are located within the receptacles 118 and are rotatable relative to the frame 108. Upper and lower curved flanges 122 and 124 extend radially outwardly from each of the relatively short rectangular portions 114. In other words, the frame 108 has two diametrically opposed pairs of flanges, each pair including a flange 122 and a flange 124. The curvature of the free ends of the flanges 122 and 124 corresponds to the curvature of the surface of the ring 112. Suitable materials for the frame 108 include plastics such as polyether ether ketone (PEEK), low-density polyethylene (LDPE), high-density polyethylene (HDPE), ultra-high-molecular-weight polyethylene (UHMWPE), polytetrafluoroethylene (PTFE) and polyamide. The frame 108 may be formed by an injection molding process or any other suitable process. In the illustrated implementation, the frame 108 is formed from molded PEEK.

Figure 6:
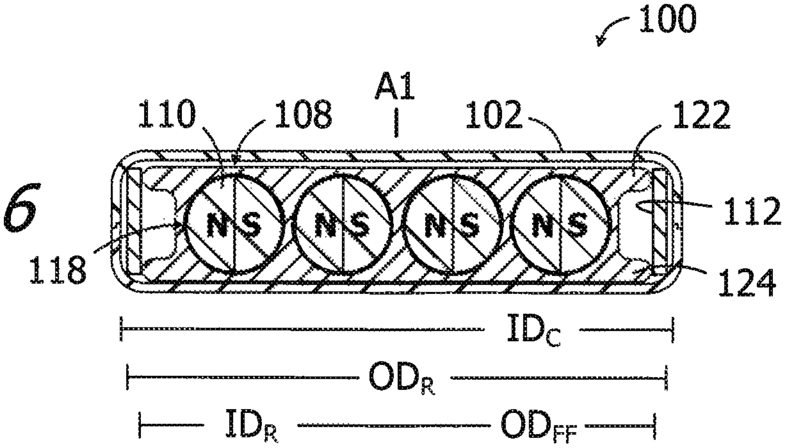
FIG. 6 is a section view taken along line 6-6 in FIG. 1.

The magnets 110 in the exemplary magnet assembly 100 are elongate diametrically magnetized magnets, two of which are relatively long and two of which are relatively short. The exemplary magnets 110 are circular in a cross-section that is perpendicular to the longitudinal axis A2 and, in some instances, may have rounded corners (as shown). Suitable materials for the magnets 110 include, but are not limited to, neodymium-boron-iron and samarium-cobalt. The magnetic attraction force between the spaced magnets 110 is such that the magnets will remain substantially aligned with one another in the N-S direction, as shown in FIG. 6, in the absence of an external magnetic field that is strong enough to rotate the magnets out of alignment. The N-S orientation of each magnet will also be perpendicular to the central axis A1 of the case 102 in the exemplary embodiment. Examples of magnetic fields that are strong enough to rotate the magnets 110 out of N-S alignment with one another are the MRI magnetic field and at least some headpiece magnetic fields.

Figure 7:
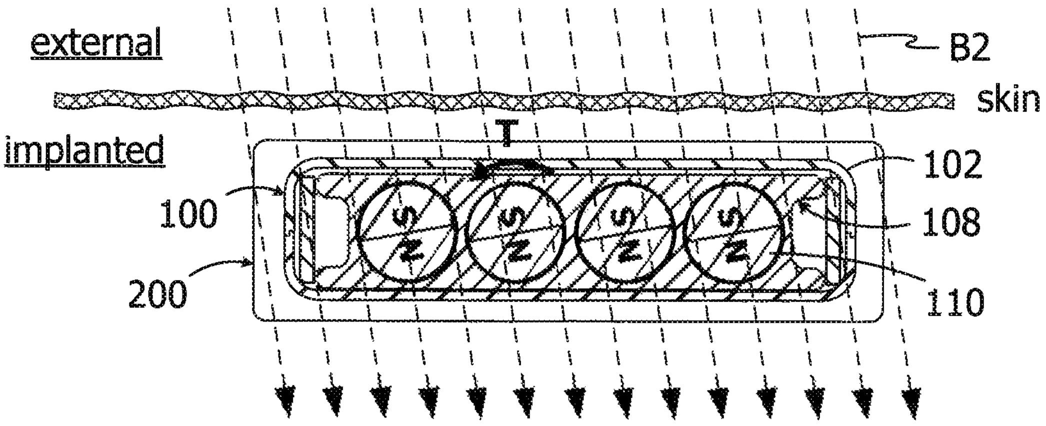
FIG. 7 is a section view similar to FIG. 6 with the implant magnet assembly in an MRI magnetic field.

To that end, and referring to FIG. 7, the exemplary magnet assembly 100 may be part of a cochlear implant 200 with a housing 202 (described below with reference to FIG. 15). When exposed to a dominant MRI magnetic field B2, the torque T on the magnets 110 will rotate the magnets about their axis A2 (FIG. 4), thereby aligning the magnetic fields of the magnets 110 with the MRI magnetic field B2. The frame 108 will also rotate about axis A1 as necessary to align the magnetic fields of the magnets 110 with the MRI magnetic field B2. When the magnet assembly 100 is removed from the MRI magnetic field B2, the magnetic attraction between the magnets 110 will cause the magnets to rotate about axis A2 back to the orientation illustrated in FIG. 6, where they are substantially aligned with one another in the N-S direction and the N-S orientation of the magnets is close to perpendicular to the central axis A1 of the case 102.

Figure 8:
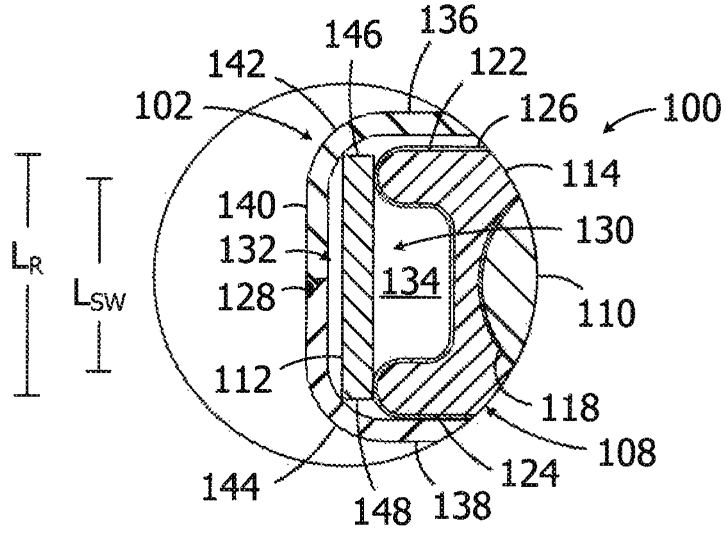
FIG. 8 is an enlarged portion of the section view illustrated in FIG. 6.
Figure 9:
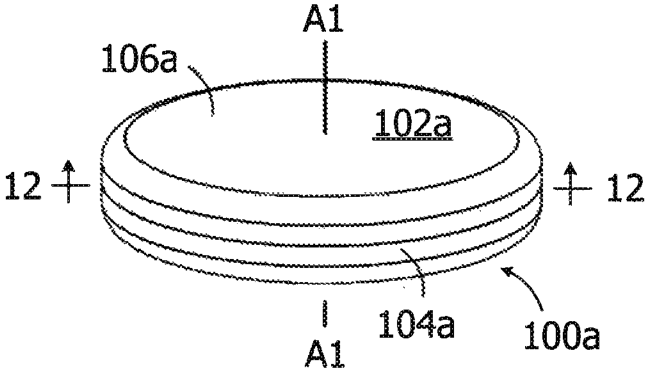
FIG. 9 is a perspective view of an implant magnet assembly in accordance with one embodiment of a present invention.
Figure 10:
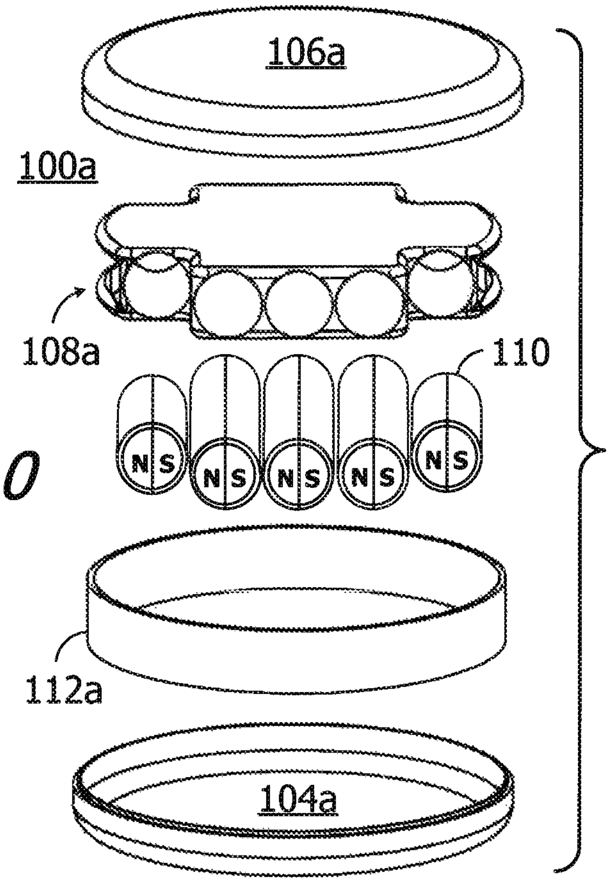
FIG. 10 is an exploded perspective view of the implant magnet assembly illustrated in FIG. 9.
Figure 11:
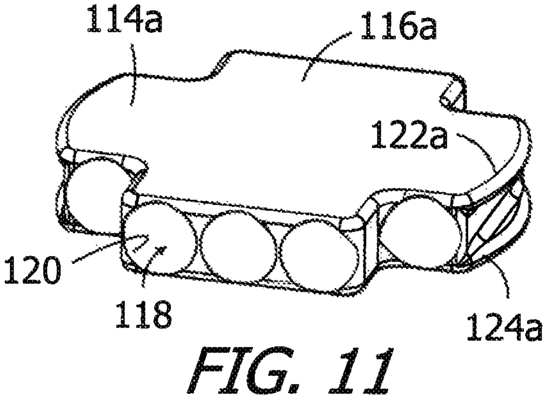
FIG. 11 is a perspective view of a portion of the implant magnet assembly illustrated in FIG. 9.

Turning to FIG. 8, friction between the frame 108 and surfaces in which it is in contact, i.e., the inner surfaces of the case 102 and ring 112, may be reduced by coating of the frame 108 with a lubricious layer 126. The tubular walls 120 that define the receptacles 118 may also include a lubricious layer in some instances, as may the inner surfaces of the case 102. The lubricious layer 126 may be in the form of a specific finish of the surface that reduces friction, as compared to an unfinished surface, or may be a coating of a lubricious material such as diamond-like carbon (DLC), titanium nitride (TiN), PTFE, polyethylene glycol (PEG), Parylene, fluorinated ethylene propylene (FEP) and electroless nickel plating sold under the tradenames Nedox® and Nedox PF™. The DLC coating, for example, may be only 0.5 to 5 microns thick. Micro-balls, biocompatible oils and lubricating powders may also be added to the interior of the case to reduce friction.

The exemplary case 102, as noted above, consists of a base 104 and a cover 106 that may be secured to one another by a weld 128 that extends around the circumference of the case. The weld 128 may be formed by a laser welding process, or other welding processes, after the frame 108 and magnets 110 have been positioned within the case 102. The frame 108, as well as magnets within the frame, may be protected from the laser beam itself, heat from the laser beam, and/or heat from the portions of the case 102 that have been heated to their melting point during the welding process by the exemplary thermal insulation arrangement 130 illustrated in FIG. 8. The exemplary thermal insulation arrangement 130 includes the ring 112 as well as air gaps 132 and 134 defined by portions of the case 102, the frame 108 and the ring 112.

Figure 4:
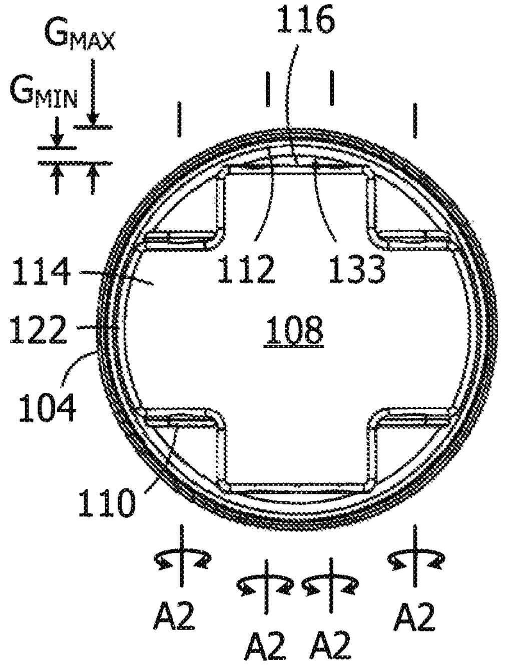
FIG. 4 is a plan view of a portion of the implant magnet assembly illustrated in FIG. 1.

To that end, the completed case 102 has end walls 136 and 138, a side wall 140, and first and second curved walls 142 and 144 that respectively connect the first and second end walls to the side wall. The end and side walls 136-140 are planar in planes defined by the axis A1 (FIG. 6), the end walls are circular in shape in planes perpendicular to the axis A1, and the side walls are annular in shape in planes perpendicular to the axis A1. The side wall 140 defines a case inner diameter $ID_C$ and a length $L_{SW}$. The ring 112 is an annular cylinder, with first and second longitudinal ends 146 and 148, that has an outer diameter $OD_R$, an inner diameter $ID_R$ and a length $L_R$. The ring outer diameter $OD_R$ is slightly less than the case inner diameter $ID_C$ (e.g., about 0.1 mm to about 0.2 mm less) and the ring length $L_R$ is slightly greater than the side wall length $L_{SW}$ (e.g., about 0.5 mm to about 0.8 mm longer). As a result, the first and second longitudinal ends 146 and 148 of the ring 112 rest against the curved walls 142 and 144, thereby creating the air gap 132 between the outer surface of the ring 112 and inner surface of case side wall 140 that extends 360 degrees around the perimeter of the ring in the illustrated embodiment. The air gaps 134 (on opposite side of the frame) are defined by the inner surface of the ring 112, the relatively short rectangular portions 114, and the curved flanges 122 and 124. The outer diameter $OD_{FF}$ of the frame 108 at the flanges 122 and 124 is substantially equal to the ring inner diameter $ID_R$ in the illustrated embodiment and, accordingly, the flanges abut the inner surface of the ring 112. Turning to FIG. 4, it should also be noted that the size and shape of the relatively long rectangular portion 116 of the frame 108 results in an air gap 133 between the inner surface of the ring 112 and the ends of the relatively long rectangular portion that varies in size from $G_{MIN}$ (about 0.23 mm) at the corners to $G_{MAX}$ (about 0.85 mm) at the center.

The air gaps 132, 133 and 134 are thermally insulative, and thereby prevent heat associated with the formation of the weld 128 from damaging the frame 108 and magnets 110, because the thermal conductivity of air is significantly less than that of the materials from which the case 102 and ring 112 are formed. For example, the thermal conductivity of titanium is 19.7 W/mK at 500° K, while the thermal conductivity of air is 0.055 W/mK at 500° K. Additional thermal insulation may also be provided by the ring 112 itself. Although the ring 112 is formed from titanium in the exemplary embodiment, other materials with lower thermal conductivity may be employed. By way of example, but not limitation, the ring 112 may be formed other metals such as stainless steel (thermal conductivity of 21.5 W/mK at 500° K), ceramics such as silicon nitride (thermal conductivity of 18 W/mK at 500° K), zirconia (thermal conductivity of 3 W/mK at 500° K) and alumina (thermal conductivity of 9 W/mK at 500° K).

Another exemplary magnet assembly is generally represented by reference numeral 100*a* in FIGS. 9-13. Magnet assembly 100*a* is substantially similar to magnet assembly 100 and similar elements are represented by similar reference numerals. For example, the magnet assembly 100*a* includes a case 102*a*, with a base 104*a* and a cover 106*a* secured by a weld 128 (FIG. 13), a frame 108*a*, a plurality of elongate diametrically magnetized magnets 110 that are rotatable relative to the frame, and a ring 112*a* that is part of the thermal insulation arrangement 130*a* discussed below with reference to FIG. 13. Here, however, the magnet assembly 100*a* includes five magnets 110, three of which are relatively long and two of which are relatively short, and the frame 108*a* includes five receptacles 118 defined by tubular walls 120. Two of the receptacles 118 are relatively short and are respectively located within the two relatively short rectangular portions 114*a*, and three of the receptacles 118 are relatively long and are located within the relatively long rectangular portion 116*a*. The frame 108*a* also includes upper and lower curved flanges 122*a* and 124*a* extend radially outwardly from each of the relatively short rectangular portions 122*a*. The curvature of the free ends of the flanges 122*a* and 124*a* corresponds to the curvature of the ring 112*a*.

Figure 12:
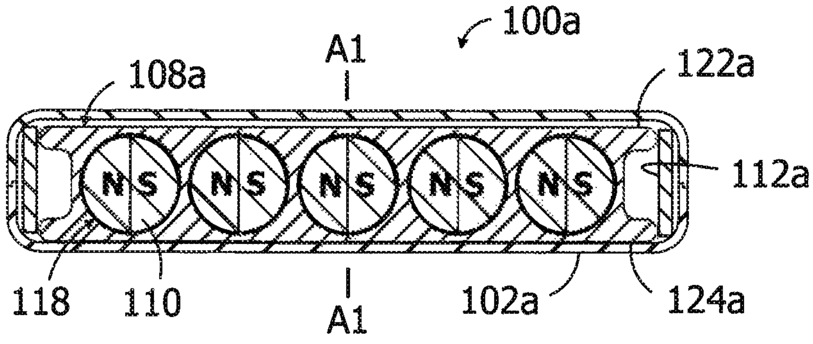
FIG. 12 is a section view taken along line 12-12 in FIG. 9.
Figure 13:
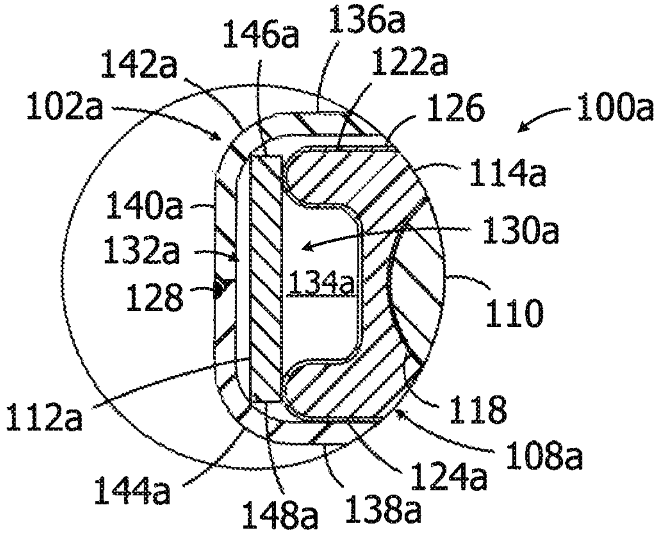
FIG. 13 is an enlarged portion of the section view illustrated in FIG. 12.

Referring more specifically to FIGS. 12 and 13, the case 102*a* may be formed by and from the methods and materials described above with reference to case 102. The case 102*a* also has end walls 136*a* and 138*a*, a side wall 140*a*, and curved walls 142*a* and 144*a* that connect the end walls to the side wall. The end and side walls 136*a*-140*a* are planar in planes defined by the axis A1. The frame 108*a* and ring 112*a* may be formed from the materials described above with reference to the 108 and ring 112. A coating 126 may be applied to the frame 108*a* in the manner described above.

The case 102*a* of the five-magnet magnet assembly 100*a* may, however, be slightly larger than the case 102 of the four-magnet assembly 100 illustrated in FIGS. 1-8 to accommodate the additional magnet and the correspondingly larger frame. In some instances, the diameter of the case 102*a* may range from 9.4 mm to 17.4 mm and the thickness may range from 1.5 mm to 3.5 mm and, in the illustrated embodiment, the diameter is about 12.6 mm and the thickness is about 3.1 mm.

The exemplary magnet assembly 100*a* also has a thermal insulation arrangement 130*a* that includes the ring 112*a* as well as air gaps 132*a* and 134*a* that are defined by portions of the case 102*a*, the frame 108 and the ring 112*a*. The respective dimensions of the case 102*a* and ring 112*a* are also such that the first and second ends 146*a* and 148*a* of the ring 112*a* rest against the curved walls 142*a* and 144*a*, thereby creating the air gap 132*a* between the ring 112*a* and case side wall 140*a* that extends around the perimeter of the ring. The air gaps 134*a* are defined by the ring 112*a*, the relatively short rectangular portions 114*a*, and the curved flanges 122*a* and 124*a*. There are also air gaps (not shown) associated with the ends of the relatively long rectangular portion 116*a*, as is described above with reference to FIG. 4.

Figure 14:
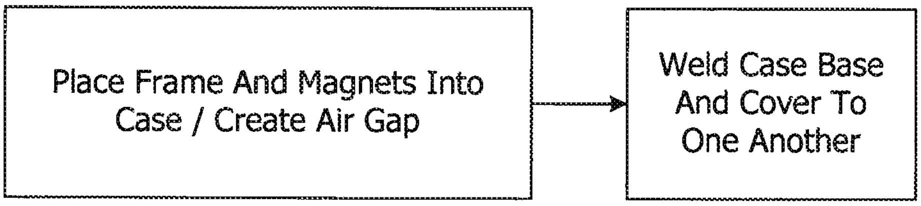
FIG. 14 is a flow chart showing a method in accordance with one embodiment of a present invention.

Turning to FIG. 14, the exemplary magnet assembly 100 (or 100*a*) may be made by a method that includes placing the frame 108 and plurality of diametrically magnetized magnets 110 into the case 102 and creating an air gap 132 between the frame and the inner surfaces of the case side wall and, thereafter, welding side wall portions of the case base 104 and cover 106 to one another.

Figure 15:
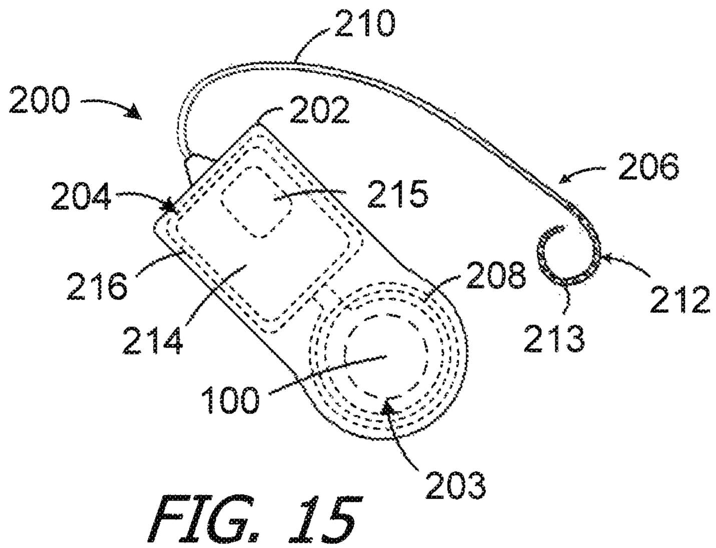
FIG. 15 is a top view of a cochlear implant in accordance with one embodiment of a present invention.

One example of a cochlear implant (or "implantable cochlear stimulator") including the present magnet assembly 100 (or 100*a*) is the cochlear implant 200 illustrated in FIG. 15. The cochlear implant 200 includes a flexible housing 202 formed from a silicone elastomer or other suitable material, a processor assembly 204, a cochlear lead 206, and an antenna 208 that may be used to receive data and power by way of an external antenna that is associated with, for example, a sound processor unit. The cochlear lead 206 may include a flexible body 210, an electrode array 212 at one end of the flexible body, and a plurality of wires (not shown) that extend through the flexible body from the electrodes 213 (e.g., platinum electrodes) in the array 212 to the other end of the flexible body. The magnet assembly 100 is located within a region encircled by the antenna 208 (e.g., within an internal pocket 203 defined by the housing 202) and insures that an external antenna (discussed below) will be properly positioned relative to the antenna 208. The exemplary processor assembly 204, which is connected to the electrode array 212 and antenna 208, includes a printed circuit board 214 with a stimulation processor 214*a* that is located within a hermetically sealed case 216. The stimulation processor 215 converts the stimulation data into stimulation signals that stimulate the electrodes 213 of the electrode array 212.

Figure 16:
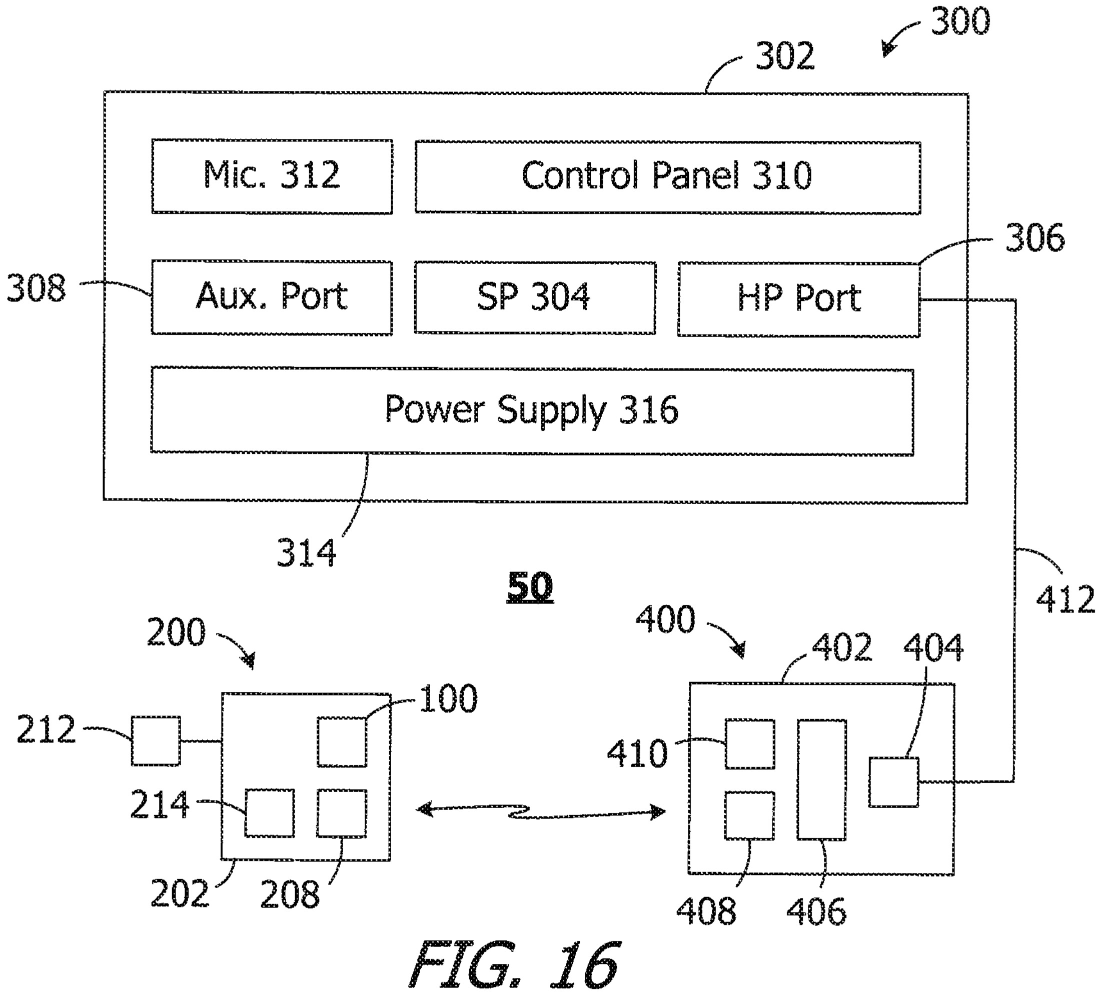
FIG. 16 is a block diagram of a cochlear implant system in accordance with one embodiment of a present invention.

Turning to FIG. 16, the exemplary cochlear implant system 50 includes the cochlear implant 200, a sound processor, such as the illustrated body-worn sound processor 300 or a behind-the-ear sound processor, and a headpiece 400.

The exemplary body worn sound processor 300 in the exemplary ICS system 50 includes a housing 302 in which and/or on which various components are supported. Such components may include, but are not limited to, sound processor circuitry 304, a headpiece port 306, an auxiliary device port 308 for an auxiliary device such as a mobile phone or a music player, a control panel 310, one or more microphones 312, and a power supply receptacle 314 for a removable battery or other removable power supply 316 (e.g., rechargeable and disposable batteries or other electrochemical cells). The sound processor circuitry 304 converts electrical signals from the microphone 312 into stimulation data. The exemplary headpiece 400 includes a housing 402 and various components, e.g., a RF connector 404, a microphone 406, an antenna (or other transmitter) 408 and an axially magnetized disk-shaped positioning magnet 410, that are carried by the housing. The headpiece 400 may be connected to the sound processor headpiece port 306 by a cable 412. The external positioning magnet 410 is attracted to the magnet assembly 100 of the cochlear stimulator 200 (see FIG. 6), thereby aligning the antenna 408 with the antenna 208. The stimulation data and, in many instances power, is supplied to the headpiece 400. The headpiece 400 transcutaneously transmits the stimulation data, and in many instances power, to the cochlear implant 200 by way of a wireless link between the antennae. The stimulation processor 215 converts the stimulation data into stimulation signals that stimulate the electrodes 213 of the electrode array 212.

In at least some implementations, the cable 412 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 312 on the sound processor 300, the microphone 406 may be also be omitted in some instances.

The functionality of the sound processor 300 and headpiece 400 may also be combined into a single head wearable sound processor that includes all of the external components (e.g., the battery, microphone, sound processor, antenna coil and magnet). Examples of head wearable sound processors are illustrated and described in U.S. Pat. Nos. 8,811,643 and 8,983,102, which are incorporated herein by reference in their entirety. Headpieces and head wearable sound processors are collectively referred to herein as "head wearable external components."

Although the inventions disclosed herein have been described in terms of the preferred embodiments above, numerous modifications and/or additions to the above-described preferred embodiments would be readily apparent to one skilled in the art. The inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A magnet assembly, comprising:

a case defining a central axis and including first and second circular end walls and an annular side wall, with an inner surface, between the first and second circular end walls;

a frame within the case and rotatable relative to the case about the central axis of the case;

a plurality of diametrically magnetized magnets that are located in the frame, that each define a longitudinal axis and a N-S direction, and that are rotatable about the longitudinal axis relative to the frame; and a ring, defining a first longitudinal end adjacent to the first circular end wall, a second longitudinal end adjacent to the second circular end wall and an outer surface the extends from the first longitudinal end to the second longitudinal end and faces the annular side wall, between the frame and the case side wall and offset from the case annular side wall such that a first air gap that extends from the first longitudinal end to the second longitudinal end, extends 360 degrees around the central axis and is located between the inner surface of the case annular side wall and the outer surface of the ring.

2. A magnet assembly as claimed in claim 1, wherein the case includes a base and a cover and a weld that secures the base and the cover to one another; and the first air gap is located between the weld and the frame.

3. A magnet assembly as claimed in claim 1, wherein the case includes a first curved wall between the first circular end wall and the annular side wall and a second curved wall between the second circular end wall and the annular side wall; and the first longitudinal end of the ring is in contact with the first curved wall and second longitudinal end of the ring is in contact with the second curved wall.

4. A magnet assembly as claimed in claim 1, further comprising:

a pair of second air gaps located between the ring and the frame.

5. A magnet assembly as claimed in claim 4, wherein the frame includes two diametrically opposed pairs of flanges, each flange including a curved free end that is in contact with the ring; and the second air gaps are located between the flanges in a respective one of the flange pairs.

6. A magnet assembly as claimed in claim 1, wherein the frame includes a plurality of spaced receptacles; and each of the receptacles has a respective one of the elongate diametrically magnetized magnets located therein.

7. A magnet assembly as claimed in claim 1, wherein the case is formed from a first material having a first thermal conductivity; and the ring is formed from a second material having a second thermal conductivity that is less than the first thermal conductivity.

8. A cochlear implant, comprising:

a cochlear lead including a plurality of electrodes;

an antenna;

a stimulation processor operably connected to the antenna and to the cochlear lead; and a magnet assembly as claimed in claim 1.

9. A cochlear implant as claimed in claim 8, further comprising:

a flexible housing;

wherein the antenna, the stimulation processor and the magnet assembly are located within the flexible housing.

10. A magnet assembly as claimed in claim 1, wherein the case includes a base and a cover that are secured to one another with a weld; and a plane that is perpendicular to the central axis passes through the weld and the air gap.

11. A magnet assembly, comprising:

a case defining a central axis and including first and second end walls and a side wall, with an inner surface and a side wall length, between the first and second end walls;

a frame within the case and rotatable relative to the case about the central axis of the case;

a plurality of diametrically magnetized magnets that are located in the frame, that each define a longitudinal axis and a N-S direction, and that are rotatable about the longitudinal axis relative to the frame; and a ring, defining an outer surface and a ring length that is greater than the side wall length, between the frame and the case side wall and offset from the case side wall such that a first air gap is located between the inner surface of the case side wall and the outer surface of the ring.

12. A magnet assembly as claimed in claim 11, wherein the case includes a base and a cover and a weld that secures the base and the cover to one another; and the first air gap is located between the weld and the frame.

13. A magnet assembly as claimed in claim 11, wherein the first air gap extends 360 degrees around the ring.

14. A magnet assembly as claimed in claim 11, further comprising:

a pair of second air gaps located between the ring and the frame.

15. A magnet assembly as claimed in claim 11, wherein the frame includes a plurality of spaced receptacles; and each of the receptacles has a respective one of the elongate diametrically magnetized magnets located therein.

16. A magnet assembly as claimed in claim 11, wherein the case is formed from a first material having a first thermal conductivity; and the ring is formed from a second material having a second thermal conductivity that is less than the first thermal conductivity.

17. A magnet assembly, comprising:

a case defining a central axis and including a base and a cover that are secured to one another with a weld, wherein a plane that is perpendicular to the central axis passes through the weld;

a frame within the case and rotatable about the central axis of the case and relative to the case;

a plurality of diametrically magnetized magnets that are located in the frame, that each define a longitudinal axis and a N-S direction, and that are rotatable about the longitudinal axis relative to the frame; and means for thermally insulating the frame from heat associated with welding the base and cover to one another by creating a first air gap through which the plane also passes and that extends completely around the central axis and a second air gap through which the plane also passes and that is located radially inward of the first air gap.

* * * * *